United States Patent [19]

Okorodudu

[11] Patent Number: 4,532,084

[45] Date of Patent: Jul. 30, 1985

[54] METHOD FOR PREPARING A METHYLENE-BIS-(O,O-DIORGANOPHOSPHORODITHIATO)-SUBSTITUTED HINDERED PHENOL

[75] Inventor: Abraham O. M. Okorodudu, West Deptford, N.J.

[73] Assignee: Mobil Oil Corporation, New York, N.Y.

[21] Appl. No.: 513,537

[22] Filed: Jul. 13, 1983

[51] Int. Cl.$^3$ ............................................. C07F 9/12
[52] U.S. Cl. ................................................... 260/978
[58] Field of Search .......................................... 260/978

[56] References Cited

U.S. PATENT DOCUMENTS 3,169,903  2/1965  Stoutamire ........................ 260/978
3,370,110  2/1968  Stoutamire ........................ 260/978

Primary Examiner—Anton H. Sutto
Attorney, Agent, or Firm—Alexander J. McKillop; Michael G. Gilman; Van D. Harrison, Jr.

[57] ABSTRACT

Method for making methylene-bis-diorganophosphorodithiato-substituted hindered phenols by conversion of hindered phenols to the corresponding hindered phenol aldehydes and subsequent reaction, without isolation, with a diorganophosphorodithioic acid, which results in economically advantageous and simplified processing as well as minimization of wasteful and costly by-products.

9 Claims, No Drawings

METHOD FOR PREPARING A METHYLENE-BIS-(O,O-DIORGANOPHOS-PHORODITHIATO)-SUBSTITUTED HINDERED PHENOL

BACKGROUND OF THE INVENTION

1. Field of the Invention

The invention relates to a method for making a phosphorus-containing hindered phenol. It more particularly relates to a method involving the conversion of a hindered phenol to a hindered phenol aldehyde and the reaction thereof, without isolation, with a diorganodithiophosphoric acid.

2. Discussion of the Prior Art

Many organic media, including lubricants and greases, hydraulic fluids for brake and transmission systems, resins and plastics for coatings and structural articles, are used under conditions that contribute to their breakdown. Oxidation of lubricants in internal combustion engines is an ever increasing problem, accelerated by the use of higher operating temperatures. The resulting oxidation produced products that may seriously interfere with lubrication.

U.S. Pat. No. 3,644,206 teaches a lubricant composition made by reacting a hindered cyclic aldehyde with a dithioic acid. No art is known, however, that teaches or suggests the method herein.

The compounds produced by the method herein are taught and claimed in U.S. Ser. No. 362,359, filed Mar. 26, 1982. The present method is an improvement over the method used in the application, however, because of the easier operation and because of the reduced production of solid thioaldehyde, polymeric and other undesirable by-products.

SUMMARY OF THE INVENTION

In accordance with the invention there is provided a method of preparing a product of the formula

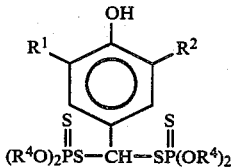

wherein $R^1$ and $R^2$ are the same or different aliphatic groups, preferably alkyl groups, containing 4 to 12 carbon atoms in any isomeric arrangement, provided that the carbon atom attached to the phenyl ring is itself bonded to at least two other carbon atoms, and $R^4$ is the same or different hydrocarbyl group containing 1 to 20 carbon atoms which comprises (1) reacting a phenol of the formula

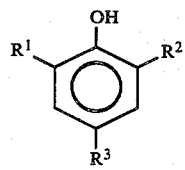

wherein $R^1$ and $R^2$ are defined herein and $R^3$ is a methyl or hydroxymethyl group in the presence of a halogen selected from chlorine and bromine, preferably the latter, and an alcohol solvent, preferably t-butyl alcohol, and (2) reacting the product of (1), without isolating it, with a phosphorodithioic acid of the formula $(R^4O)_2PSSH$ wherein $R^4$ is defined herein.

"Hydrocarbyl", as used herein, shall mean alkyl, alkenyl, aryl, aralkyl, alkaryl and cycloalkyl, where the aryl portion has 6 to 14 carbon atoms (e.g., phenyl, naphthyl and anthryl). The aliphatic groups are preferably t-alkyl groups.

DESCRIPTION OF SPECIFIC EMBODIMENTS

In general, the reaction between hindered phenol aldehyde and phosphorodithioic acid is as follows

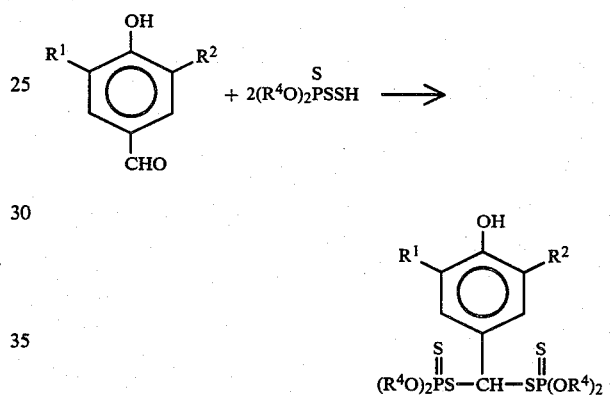

wherein $R^1$, $R^2$, $R^3$ and $R^4$ are as defined hereinabove.

Using the general reaction, it has been found that when starting the reaction by combining aldehyde with the phosphorodithioic acid in the reaction mixture reduced yields are obtained due to excessive yield of a dimer, trimer or both. The mechanism of the reaction which produces the dimer or timer is believed to be as follows.

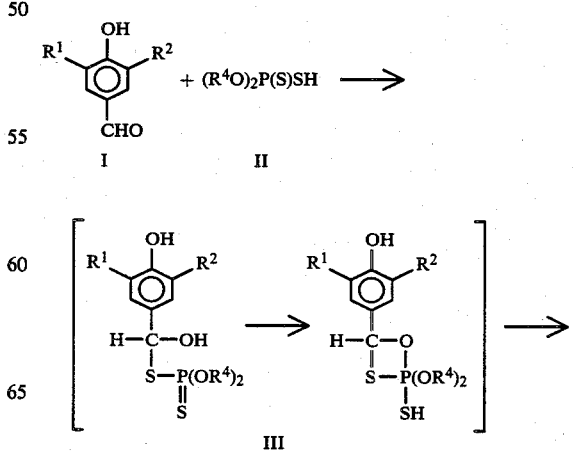

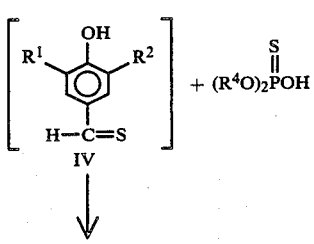

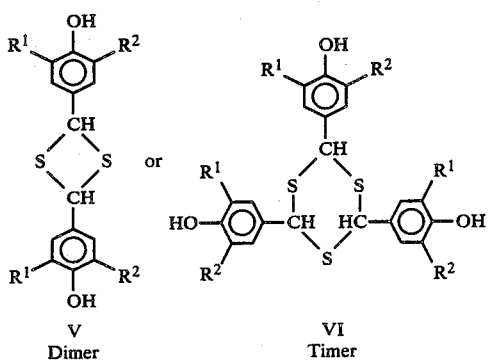

In the above reaction, the intermediate hemithioacetal III either reacts with another mole of the phosphorodithioic acid to give the desired useful hindered phenol product or forms the unstable thiobenzaldehyde which readily dimerizes or trimerizes to give the solid product which is wasteful and not useful for the improvement of lubricants.

We have found that the product can be made directly from a hindered phenol reactant without isolating the desired aldehyde, and with greater facility and less of the wasteful by-product. This is done by oxidizing, for example, di-t-butyl-p-cresol (DBPC) or di-t-butyl-4-hydroxybenzyl alcohol with bromine, followed by reaction, in situ, of the hindered aldehyde formed with the phosphorodithioic acid. This reaction scheme may be shown as follows:

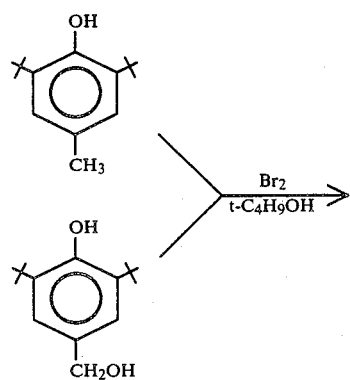

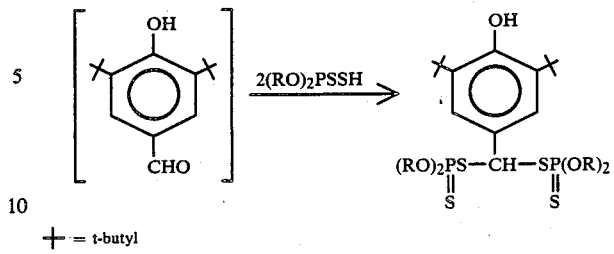

$+ = $ t-butyl

As already indicated, although the dimer/trimer by-product may also be formed, it is formed to a considerably lesser extent by the method of this invention.

Thus, the manufacture of the additives of the invention can be smoothly and economically carried out in a single reactor using a single solvent, in a relatively much shorter time to give high yields of useful products, very low yields of undesirable by-products, and acceptable performance and properties. In the course of these operations the DBPC or hydroxymethyl hindered phenol is substantially converted to the corresponding formylated reactant, but any minor amounts of other phenolic side products which are formed and any unreacted DBPC which remains are not deleterious to the properties and performance of the subject lubricant additives. The preferred hindered phenol is 2,6-di-tert-butyl-4-methylphenol or 2,6-di-tert-butyl-4-hydroxymethylphenol. Others that may be employed include those wherein $R^1$ and $R^2$ may be the same or different and are selected from butyl, hexyl, octyl, decyl or dodecyl groups and wherein in any hindered phenol selected, $R^3$ is methyl or hydroxymethyl.

The oxidation of the hindered phenol in situ by bromine or chlorine is carried out using a molar ratio of such halogen to the hindered phenol of from about 0.5 to 1 to about 3 to 1. Preferably the molar ratio of halogen to hindered phenol is from about 1 to 1 to about 2.5 to 1. The solvent for the oxidation step and for the subsequent reaction with the phosphorodithioic acid is an alcohol, ranging from about 3 carbon atoms to about 6 carbon atoms, which is capable of forming a stable or transient hypobromite. Included in such solvents are 2-propyl alcohol, isobutyl alcohol, t-butyl alcohol, neopentyl alcohol, isoamyl alcohol, n-hexyl alcohol and the like. The preferred solvent is t-butyl alcohol. The temperature may range during the addition of halogen to the hindered phenol from about 5° C. to about 50° C., with the preferred temperature range being from about 20° C. to about 40° C. The molar ratio of the phosphorodithioic acid to the hindered phenol aldehyde formed in situ (assuming total conversion of the hindered phenol) is from about 1.25 to 1 to about 2.6 to 1, with the preferred molar ratio being from about 2 to 1. The temperature range for the addition of the phosphorodithioic acid to the oxidized hindered phenol may range from 30° C. to 160° C., with the preferred range being from about 50° to 90° C. The time required for each step is not critical, but ranges from about 1 hour to about 3 hours, with about 1.25 hours to 2.5 hours preferred for the bromine reaction step and from about 2 to about 6 hours, preferably from about 2.5 hours to about 4 hours, for the phosphorodithioic acid addition step.

The phosphorodithioic acids can be made easily by the prior art method of reacting the appropriate alcohol with phosphorus pentasulfide. The alcohols that may be used to prepare the acid include butyl alcohol, hexyl alcohol, octyl alcohol, decyl alcohol, dodecyl alcohol, tetradecyl alcohol, hexadecyl alcohol and octadecyl alcohol and mixtures thereof. It will be understood that the useful phosphorodithioic acids include any acid made for these in any combination.

Having described the invention in general detail, the following example will provide specific illustrations thereof. It is understood that it is illustrative only and that the invention is not to be limited thereby.

EXAMPLE

To a stirred solution of 2,6-di-tert-butyl-4-methylphenol (110 g) in tert-butyl alcohol (600 ml) cooled at 22° C., bromine (160 g) was added during 1.5 hr. at such a rate as to maintain the reaction temperature at 22° C., using ice bath cooling. After addition, the mixture was purged of any unreacted bromine by sub-surface sparging with nitrogen while the temperature was raised during 0.5 hr. to 42° C.

Addition of 0,0-di(4-methyl-2-pentyl) phosphorodithioic acid (298 g) to the stirred reaction mixture was begun at 42° C. and completed during 0.67 hr. while the temperature was raised to 73° C. by heating. The reaction temperature was maintained at 73° C. for 3 additional hours and the mixture was cooled and stirred with 20% sodium carbonate solution (1000 ml). Petroleum ether was added to assist separation and the mixed organic-aqueous layers were filtered to remove white solid thioaldehyde dimer (5 g).

The organic layer of the filtrate was separated, water washed, dried, and stripped to yield 392 grams of product, obtained as a moderately viscous oily liquid.

The preferred reaction scheme involves a one-pot method in which oxidation to the aldehyde and reaction thereof with acid are carried out without intermediate separation of the hindered phenol aldehyde. In the preferred method DBPC in t-butyl alcohol is oxidized by bromine, or t-butyl hypobromite formed in situ, to the corresponding aldehyde and converted without isolation to the product (as defined hereinabove) by addition to the same reactor of 0,0-di-(4-methyl-2-pentyl)phosphorodithioic acid.

We claim:

1. A method of preparing a product of the formula

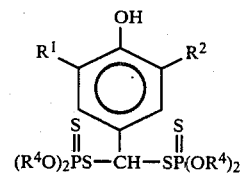

wherein $R^1$ and $R^2$ are the same or different aliphatic groups containing 1 to 20 carbon atoms and $R^4$ is selected from hydrocarbyl groups containing 4 to 18 carbon atoms by (1) reacting a hindered phenol of the formula

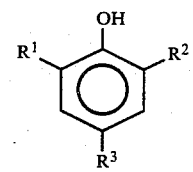

wherein $R^1$ and $R^2$ are defined herein and $R^3$ is a methyl or hydroxymethyl group, in the presence of an alcohol, having from 3 to 6 carbon atoms, and a halogen selected from chlorine and bromine, the reaction taking place at from about 5° C. to about 50° C. using a molar ratio of halogen to hindered phenol of from about 0.5 to 1 to about 3 to 1, and (2) without isolating the product thus formed, reacting same with a phosphorodithioic acid of the formula $(R^4O)_2PSSH$ wherein $R^4$ is defined herein, this latter reaction being run at from about 30° C. to about 160° C. using a molar ratio of phosphorodithioic acid to product of reaction (1) of from about 1.25 to 1 to about 2.6 to 1.

2. The method of claim 1 wherein said hydrocarbyl groups are alkyl, aryl, alkenyl, aralkyl, alkaryl or cycloalkyl groups.

3. The method of claim 2 wherein the aryl portion contains from 6 to 14 carbon atoms.

4. The method of claim 1 wherein the aliphatic group is a tertiary alkyl group.

5. The method of claim 4 wherein the tertiary alkyl group is the t-butyl group.

6. The method of claim 1 wherein the halogen is bromine.

7. The method of claim 1 wherein said hindered phenol is 2,6-di-t-butyl-4-methylphenol, said halogen is bromine, said alcohol is t-butyl alcohol and said phosphorodithioic acid is 0,0-di-(4-methyl-2-pentyl) phosphorodithioic acid.

8. The method of claim 1 wherein the alcohol is 2-propyl alcohol, isobutyl alcohol, t-butyl alcohol, neopentyl alcohol, isoamyl alcohol or n-hexyl alcohol.

9. The method of claim 8 wherein the alcohol is t-butyl alcohol.

* * * * *